United States Patent [19]

de Mul

[11] 4,035,918
[45] July 19, 1977

[54] DENTAL INSTRUMENT
[76] Inventor: Erik François Johannes de Mul, Woerdsestraat 7, Ressen, Netherlands
[21] Appl. No.: 643,851
[22] Filed: Dec. 23, 1975
[30] Foreign Application Priority Data
  Dec. 27, 1974  Netherlands .................. 7416952
[51] Int. Cl.² .................................... A61C 3/08
[52] U.S. Cl. ............................................ 32/54
[58] Field of Search .................. 32/54, 40 A; 81/1
[56] References Cited
U.S. PATENT DOCUMENTS
  3,286,558  11/1966  Hufnagel .................................. 81/1
  3,816,922   6/1974  Thiel ....................................... 32/54

*Primary Examiner*—G.E. McNeill
*Attorney, Agent, or Firm*—Depaoli & O'Brien

[57] ABSTRACT

A dental instrument for pressing down fillings of amalgam or a different tooth filling material, comprising a head with a through-bore, impact means for axial reciprocal movement in the bore, a handle, the main direction of which includes an angle with the impact direction, and at least one additional head with through-bore and appurtenant impact means adapted to reciprocate axially in the bore of said additional head, the impact direction of each additional impact means including an angle with both the main direction of the handle and with the impact direction of the first impact means, while the impact surfaces of said impact means differ in size, shape, position, etc.

17 Claims, 3 Drawing Figures

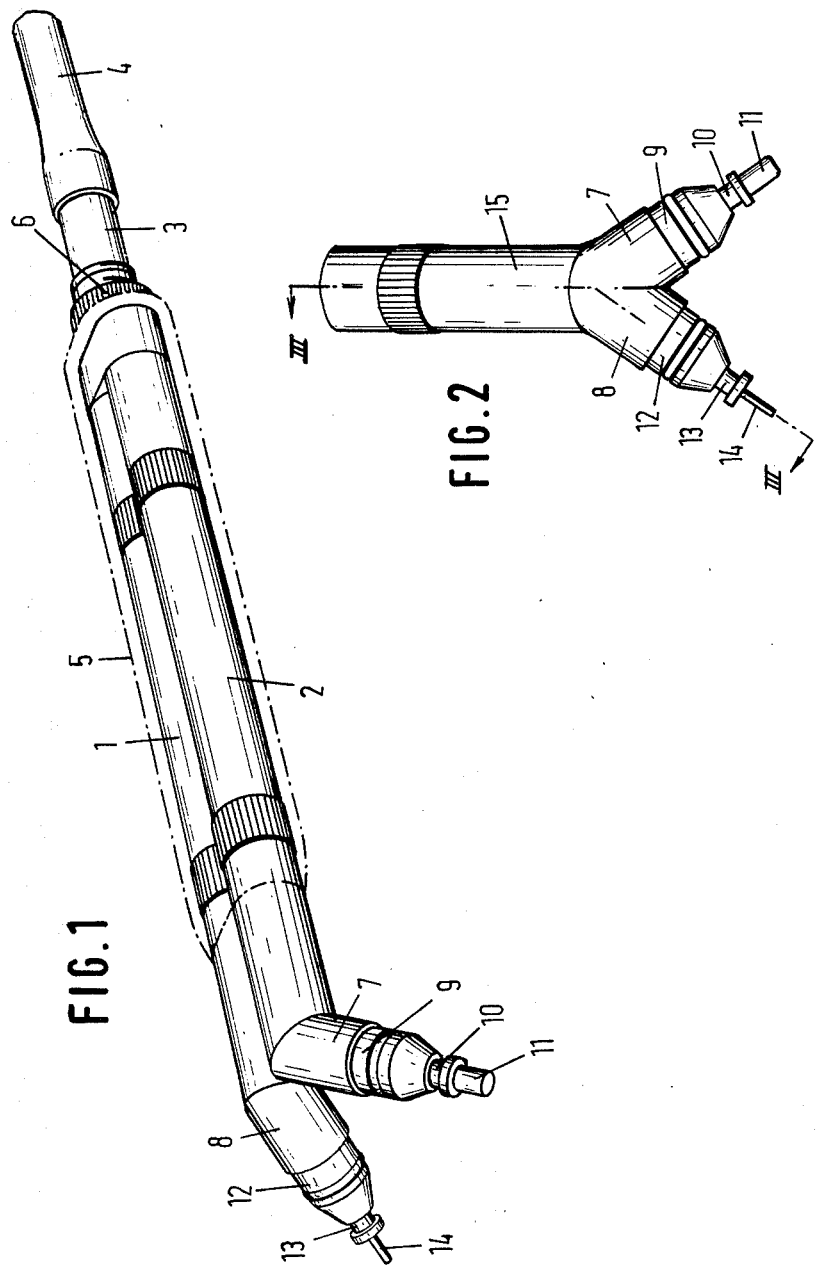

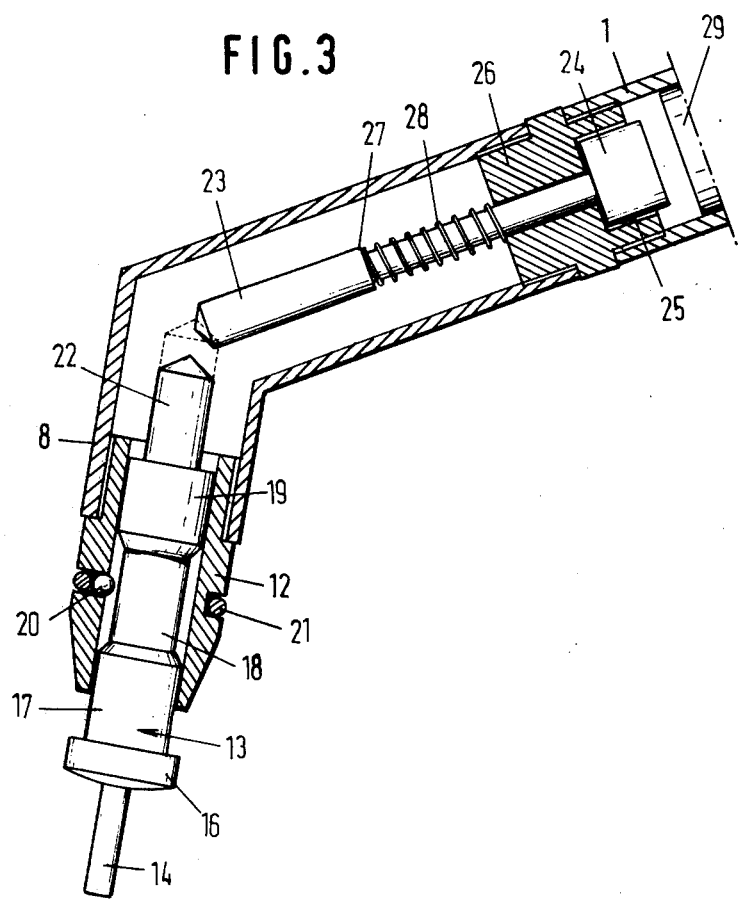

DENTAL INSTRUMENT

The present invention relates to a dental instrument for pressing down fillings of amalgam or different tooth filling material, comprising a head with a through-bore, impact means for axial reciprocal movement in the bore, and a handle, the main direction of which forms an angle with the impact direction.

In such a known dental instrument the impact means formed by a pin should be exchanged for a thinner pin and vice versa during use in order to press down the inserted amalgam filling properly in every crevice of the dental cavity and not to punch holes therein too easily. These exchanges, during which the dental instrument must be removed from the mouth, have to be effected several times for one filling and may amount to some hundreds of times a day, so that these exhanges take a considerable time, therefore.

The object of the invention is to reduce this exchanging time so as to perform the dental treatment more efficiently.

With a dental instrument of the type referred to above this is achieved, according to the invention, by at least one additional head with through-bore and appurtenant impact means adapted to reciprocate axially in the bore of said additional head, the impact direction of each additional impact means including an angle with both the main direction of the handle and with the impact direction of the first impact means, while the impact surfaces of said impact means differ in size, shape, position, etc. If during use of the dental instrument according to the invention the impact means should be exchanged, this can be done by simply turning the hand. Also removal of one pin from the head and replacing it by a different pin is no longer necessary. The dental instrument need no longer be removed from the patient's mouth row, as a result of which the exchanging time is reduced to a minimum.

According to a preferred embodiment of the invention the dental instrument is so constructed that the angle between the impact direction of each additional impact means and the handle is equal to that between the impact direction of the first impact means and the handle.

By selecting this position for the impact means, the impact surfaces lie almost entirely on a circle, the plane of which is perpendicular to the main direction of the handle and the centre of which forms part of that median of the handle which runs parallel to the main direction.

For an optimum handling of the dental instrument according to the invention it is preferred, according to a further embodiment of the dental instrument according to the invention, that at least two heads are mounted on a single, cylindrical holder, so that a compact construction of the dental instrument according to the invention is obtained.

The dental instrument according to the invention will now be elucidated in more detail with reference to the drawings showing some embodiments.

FIG. 1 shows a perspective side elevational view of the dental instrument according to the invention;

FIG. 2 shows a perspective front elevational view of a further embodiment of the dental instrument according to the invention; and FIG. 3 shows a sectional view on the line III—III in FIG. 2.

The dental instrument according to the invention shown in perspective view in FIG. 1 comprises a hollow cylindrical holder 1 and a similar cylindrical holder 2. The two holders 1, 2 are interconnected by means of a connecting piece 3 and connected to one end of a flexible hose 4. The other end of hose 4 is connected to a pneumatic pulsation source not shown. For easy handling of the two holders 1, 2 they can be embraced by a handgrip 5 shown in chain line, which can be resiliently clamped on the two holders 1, 2 or locked thereto by means of a nut 6. Holders 1, 2, coupling piece 3 and handgrip 5 then form together the handle of the dental instrument. Between the coupling piece and the hose there may moreover be provided a control device by means of which the magnitude of the vibration can be adjusted to a desired value.

The two containers 1, 2 each have a hollow, cylindrical head 7, 8 at their end opposed to coupling piece 3. The axis of holder 1 encloses an angle with the axis of head 7, as does the axis of holder 2 with that of head 8, the enclosed angles being equal. Further the axes of both heads 7, 8 enclose an angle of, for example, approximately 70°.

In the mouth of head 7 there is provided a sleeve 9, which is connected to head 7, for example by means of thread or by force fit. Sleeve 9, which tapers conically at its end opposing head 7, is provided with an axial through-bore, in which impact means 10 is axially reciprocable with a sliding fit. Impact means 10 has a pin 11 at its end projecting from sleeve 9, the free end face of which serves as an impact surface.

The head 8 contains a sleeve 12 with impact means 13 therein, which are identical to sleeve 9 and impact means 10. Also in this head the impact means has at one end a pin 14, the end face of which serves as an impact surface. Pin 14 has a smaller diameter than pin 11, however. The operation and drive of impact means 10 and 13 will be discussed hereinafter.

With the aid of the above dental instrument it is possible to press down fillings with a larger diameter pin and a smaller diameter pin without exchanging the instrument or auxiliary instrument and without removing the instrument from the patient's mouth. For the exchange of impact means it is only necessary to make a simple turning movement of the hand, after which the pressing down can directly be continued.

FIG. 2 shows a further, preferred embodiment of the dental instrument according to the invention. The difference with the instrument shown in FIG. 1 resides in the use of a single handle 15, on one end of which two heads are mounted and the other end of which is connected via a flexible hose to a pulsation source. The heads are further identical to those shown in FIG. 1 and consequently have the same reference numerals. The use of a single holder makes the instrument considerably more compact. As such an instrument is used in the mouth of a patient, this means that the handling of the instrument is considerably facilitated.

FIG. 3 is a sectional view through a head used in the dental instrument shown in FIGS. 1 or 2. Impact means 13, axially reciprocable in sleeve 12, includes pin 14, a head 16 and cylinders 17, 18 and 19, which parts form a unitary portion. Cylinders 17 and 19 have the same diameter, which is such as to form a sliding fit together with the inner diameter of sleeve 12. Impact means 13 is retained in sleeve 12 and the axial impact length is controlled by the narrowed part 18 cooperating with a pin 20, present in a radial bore in sleeve 12 and locked by a spring washer 21 disposed in an annular recess in sleeve 12. The free end 22 of cylinder 19 tapers conically and can cooperate with the free end of a vibratory pin 23, the other end of which is connected to a buffer block 24. This buffer block 24 is disposed in a recess 25 of a guide body 26, which is rigidly connected to holder 1. Guide body 26 is further provided with an axial bore through which the vibratory pin 23 extends with sliding fit. Vibratory pin 23 has from some distance from the free end up to its other end a smaller diameter, as a result of which a stop shoulder 27 is formed. Against this stop shoulder 27 one end of a compression spring 28 finds support, the other end of which strikes against the guide body 26. Inside the hollow, cylindrical holder 1 there is furthermore provided a — partly shown — pneumatically pulsating piston 29, which can cooperate with buffer block 24.

The operation of the instrument described above is as follows:

To press down the filling, the instrument is introduced into the mouth of the patient and pressed with pin 14 on the filling to be made. Impact means 13 is thereby pressed further into sleeve 12 till for example the free end 22 is in the position shown by a broken line. Owing to this displacement of impact means 13 the vibratory pin 23 is pressed backwardly against the action of compression spring 28, so that buffer block 24 is released from guide body 26. The continuously pulsatorily driven piston 29 will now impose a reciprocal vibration on the vibratory pin 23 and the coacting impact means 13, as a result of which the filling to be made is pressed down. As soon as the pressure on pin 14 is removed, it will get out of contact with vibratory pin 23, which in turn will assume its forward position through the action of compression spring 28. Consequently the drive of impact means and vibratory pin is stopped.

It can easily be derived from the foregoing that if several heads with appurtenant impact means are mounted on a single holder, all impact means can be driven independently with this system, because the cone surface of vibratory pin 23 can also cooperate with the conical surface of a different impact means, since each time only one impact means is caused to vibrate.

The dental instruments described above and shown in the drawings serve exclusively to elucidate the essence of the invention. It will be clear that many variants and modifications are possible without departing from the scope of the present invention. For example, the use of a handle comprising more than two heads, a drive by means of a micromotor or an electro-magnetic drive may be considered.

I claim:

1. A dental instrument for packing fillings of amalgam, including a handle with a bored head having an axially disposed bore and a first impact means which is axially reciprocable in said bore by selective contact with a driving device which is axially reciprocable within said handle, said bored head being disposed in a direction which encloses an angle with the axis of said handle, characterized in that said handle includes at least one second bored head and second impact means adapted to be axially reciprocated by said driving device, the impact direction of each said second impact means including an angle with both said axis of said handle and with the impact direction of said first impact means, said first and second impact means being each kept out of contact with said driving device by a biasing means and being separately brought into said selective contact with said driving device by exercising a compressive force on one said bored head.

2. A dental instrument according to claim 1, characterized in that said angle between said impact direction of each second impact means and said handle is equal to that between said impact direction of said first impact means and said handle.

3. A dental instrument for packing tooth filling materials into an excavated portion of a tooth, comprising:
   A. an elongated handle, comprising:
      1. a pulsating means for imparting pulsating movement,
      2. an axially reciprocable vibratory pin, having:
         a. at its inner end, a buffer means for selectively engaging said pulsating means and receiving said pulsating movement,
         b. at the outer end, an impact means for selectively transmitting said pulsating movement through a selected angle, and
         c. a biasing means for axially spacing apart said pulsating means and said buffer means, and
      3. a pin guide means for slideably aligning and supporting said axially reciprocable vibratory pin and for controlling said spacing apart of said pulsating means and said buffer means; and
   B. an impact head, comprising:
      1. an axially reciprocable cylinder which is disposed at said selected angle to the axis of said axially reciprocable vibratory pin, comprising:
         a. at its inner end, an inclined impact receiving surface which is adapted to engage said impact means, and
         b. at its outer end, an impact pin, and
      2. a cylinder guide means for slideably aligning and supporting said axially reciprocable cylinder.

4. The dental instrument of claim 3, wherein said pulsating movement is transmitted to said impact pin when said impact pin is pressed against said tooth filling materials with sufficient pressure to press said inclined impact receiving surface against said impact means and to press said buffer means against said pulsating means.

5. The dental instrument of claim 4, wherein said impact head further comprises a stroke control means for controlling the impact length of said pulsating movement.

6. The dental instrument of claim 5, wherein said impact means is capable of selectively transmitting said pulsating movement through at least two said selected angles to at least two said impact heads which are disposed in at least two directions that are angularly separated.

7. The dental instrument of claim 6, wherein said at least two impact heads are angularly separated by an angle of 70°.

8. The dental instrument of claim 4, wherein said impact means has an impact transmitting surface which is disposed in parallel to said impact receiving surface.

9. The dental instrument of claim 8, wherein said impact transmitting and receiving surfaces engage slidingly while transmitting said pulsating movement.

10. The dental instrument of claim 9, wherein said angle between said impact transmitting surface and said axis of said vibratory pin is equal to the angle between said impact receiving surface and the axis of said axially reciprocable cylinder.

11. The dental instrument of claim 5, wherein said stroke control means comprises:

A. a radially recessed cylinder which is axially and centrally disposed along said axially reciprocable cylinder;
B. a pair of circumferentially disposed shoulders which endwise straddle said radially recessed cylinder; and
C. a pin which is rigidly attached to said handle and disposed radially inwardly of said shoulders, whereby pulsating movement of said axially reciprocable cylinder causes said shoulders to strike said pin alternately, the length of said recessed cylinder controlling said impact length.

12. The dental instrument of claim 6, wherein said at least two impact heads are three said impact heads, separated by three said selected angles, which are capable of selectively receiving said pulsating movement from said impact means.

13. The dental instrument of claim 9, wherein said impact transmitting and receiving surfaces are conical surfaces.

14. In a dental instrument having a pulsating means for imparting pulsating movement within a handle and a plurality of axially reciprocable impact pins for selectively pressing down a filling of amalgam, the improvement comprising a pressure-responsive transmission means for selectively transmitting said pulsating movement through a selected angle to a selected impact pin of said plurality of impact pins, said transmission means comprising a single impact transmitting surface and a plurality of receiving surfaces which are disposed in parallel and engage slidingly while transmitting said pulsating movement.

15. The improvement in the dental instrument of claim 14, wherein said impact transmitting and receiving surfaces are conical surfaces, said conical impact transmitting surface being connected to said pulsating means and each said conical impact receiving surface being connected to one of said plurality of impact pins.

16. The improvement in the dental instrument of claim 15, wherein said pressure-responsive transmission means is actuated by pressing said selected impact pin against said filling of amalgam, whereby the conical impact receiving surface connected therewith is slideably moved into intermittent contact with said conical impact transmitting surface.

17. The improvement in the dental instrument of claim 15, wherein said plurality of impact receiving surfaces lie substantially on a circle, the plane of which is perpendicular to the main direction of said handle and the centre of which is along the axis of said handle.

* * * * *